US007650204B2

(12) United States Patent
Dariush

(10) Patent No.: US 7,650,204 B2
(45) Date of Patent: Jan. 19, 2010

(54) ACTIVE CONTROL OF AN ANKLE-FOOT ORTHOSIS

(75) Inventor: Behzad Dariush, Sunnyvale, CA (US)

(73) Assignee: Honda Motor Co., Ltd., Tokyo (JP)

( * ) Notice: Subject to any disclaimer, the term of this patent is extended or adjusted under 35 U.S.C. 154(b) by 602 days.

(21) Appl. No.: 11/402,487

(22) Filed: Apr. 11, 2006

(65) Prior Publication Data
US 2006/0270950 A1 Nov. 30, 2006

Related U.S. Application Data

(63) Continuation-in-part of application No. 11/395,654, filed on Mar. 30, 2006, which is a continuation-in-part of application No. 11/038,691, filed on Jan. 19, 2005, which is a continuation-in-part of application No. 11/038,692, filed on Jan. 19, 2005, which is a continuation-in-part of application No. 11/038,978, filed on Jan. 19, 2005, and a continuation of application No. 10/151,647, filed on May 16, 2002.

(60) Provisional application No. 60/667,518, filed on Apr. 1, 2005, provisional application No. 60/670,732, filed on Apr. 12, 2005, provisional application No. 60/301,891, filed on Jun. 29, 2001, provisional application No. 60/353,378, filed on Jan. 31, 2002.

(51) Int. Cl.
G06F 19/00 (2006.01)
(52) U.S. Cl. .................. 700/245; 600/587; 600/595; 601/27; 601/33; 601/34; 601/35; 602/28; 700/247; 700/260; 700/261
(58) Field of Classification Search .................. 623/24, 623/47, 50; 602/26; 192/81 C; 73/862.08; 482/1; 600/587, 595; 601/27, 33, 34, 35; 700/245, 247, 260, 261
See application file for complete search history.

(56) References Cited

U.S. PATENT DOCUMENTS 4,244,120 A 1/1981 Harris (Continued)

FOREIGN PATENT DOCUMENTS

| EP | 1422128 A | 5/2004 |
| JP | 2000-249570 | 9/2000 |
| RU | 2 107 328 C1 | 3/1998 |

(Continued)

OTHER PUBLICATIONS

"Berkeley Researchers Developing Robotic Exoskeleton That Can Enhance Human Strength and Endurance,"ScienceDaily LLC, 1995-2004, [online] [Retrieved on Oct. 9, 2006] Retrieved from the Internet<URL:http://bleex.me.berkeley.edu/bleexhistPDFs/sciencedaily.pdf>.

(Continued)

Primary Examiner—Khoi Tran
Assistant Examiner—Stephen Holwerda
(74) Attorney, Agent, or Firm—Fenwick & West LLP; Mark Duell

(57) ABSTRACT

Techniques are provided for controlling a human-exoskeleton system including an ankle-foot orthosis by receiving system parameters for the human-exoskeleton system, receiving generalized coordinates such as an orientation of the foot, and determining a joint torque for controlling the ankle-foot orthosis to compensate for one or more components of forces acting on the foot. Forces selected for compensation include gravitational forces as well as external forces such as ground reaction forces. Techniques are provided for determining an ankle joint torque for partial or complete compensation of forces acting on the foot about an axis of rotation. The provided techniques mitigate the amount of interference between voluntary control and assist control, thereby allowing humans to quickly humans adapt to an exoskeleton system.

21 Claims, 7 Drawing Sheets

U.S. PATENT DOCUMENTS

| | | |
|---|---|---|
| 4,786,847 A | 11/1988 | Daggett et al. |
| 4,834,200 A | 5/1989 | Kajita |
| 5,044,360 A | 9/1991 | Janke |
| 5,136,227 A | 8/1992 | Nakano et al. |
| 5,203,346 A | 4/1993 | Fuhr et al. |
| 5,247,432 A | 9/1993 | Ueda |
| 5,323,549 A | 6/1994 | Segel et al. |
| 5,362,288 A | 11/1994 | Razon |
| 5,432,417 A | 7/1995 | Takenaka et al. |
| 5,459,659 A | 10/1995 | Takenaka |
| 5,570,286 A | 10/1996 | Margolis et al. |
| 5,625,577 A | 4/1997 | Kunii et al. |
| 5,659,480 A | 8/1997 | Anderson et al. |
| 5,706,589 A | 1/1998 | Marc |
| 5,808,433 A | 9/1998 | Tagami et al. |
| 5,835,693 A | 11/1998 | Lynch et al. |
| 5,942,869 A | 8/1999 | Katou et al. |
| 5,982,389 A | 11/1999 | Guenter et al. |
| 6,045,524 A | 4/2000 | Hayashi et al. |
| 6,076,025 A | 6/2000 | Ueno |
| 6,152,890 A | 11/2000 | Kupfer et al. |
| 6,161,080 A | 12/2000 | Aouni-Ateshian et al. |
| 6,289,265 B1 | 9/2001 | Takenaka et al. |
| 6,445,983 B1 | 9/2002 | Dickson et al. |
| 6,505,096 B2 | 1/2003 | Takenaka et al. |
| 6,580,969 B1 | 6/2003 | Ishida et al. |
| 6,633,783 B1 | 10/2003 | Dariush et al. |
| 6,640,160 B2 | 10/2003 | Takahashi et al. |
| 6,750,866 B1 | 6/2004 | Anderson, III |
| 6,766,204 B2 | 7/2004 | Niemeyer et al. |
| 6,785,591 B1 | 8/2004 | Hansson |
| 6,915,150 B2 | 7/2005 | Cinquin et al. |
| 6,943,520 B2 | 9/2005 | Furuta et al. |
| 7,010,390 B2 | 3/2006 | Graf et al. |
| 7,013,201 B2 | 3/2006 | Hattori et al. |
| 7,024,279 B2 | 4/2006 | Rose, III et al. |
| 7,112,938 B2 | 9/2006 | Takenaka et al. |
| 7,135,003 B2 * | 11/2006 | Dariush .................. 600/595 |
| 7,184,858 B2 | 2/2007 | Okazaki et al. |
| 7,191,036 B2 | 3/2007 | Takenaka et al. |
| 7,260,450 B2 | 8/2007 | Okazaki et al. |
| 7,278,954 B2 * | 10/2007 | Kawai et al. .................. 482/1 |
| 7,333,111 B2 | 2/2008 | Ng-Thow-Hing et al. |
| 2003/0018283 A1 | 1/2003 | Dariush |
| 2003/0023415 A1 | 1/2003 | Nakamura et al. |
| 2003/0115031 A1 | 6/2003 | Dariush et al. |
| 2004/0031169 A1 | 2/2004 | Jensen et al. |
| 2004/0102723 A1 | 5/2004 | Horst |
| 2004/0107780 A1 | 6/2004 | Kawai et al. |
| 2004/0116836 A1* | 6/2004 | Kawai et al. ............. 600/595 |
| 2004/0158175 A1 | 8/2004 | Ikeuchi et al. |
| 2004/0193318 A1 | 9/2004 | Ito |
| 2004/0249319 A1 | 12/2004 | Dariush |
| 2004/0254771 A1 | 12/2004 | Riener et al. |
| 2005/0070834 A1* | 3/2005 | Herr et al. ................. 602/28 |
| 2005/0102111 A1 | 5/2005 | Dariush et al. |
| 2005/0104548 A1 | 5/2005 | Takenaka et al. |
| 2005/0209535 A1 | 9/2005 | Dariush |
| 2006/0046909 A1 | 3/2006 | Rastegar et al. |
| 2006/0100818 A1 | 5/2006 | Nakamura et al. |
| 2006/0139355 A1 | 6/2006 | Tak et al. |
| 2006/0173578 A1* | 8/2006 | Takenaka et al. ........... 700/245 |

FOREIGN PATENT DOCUMENTS

| | | |
|---|---|---|
| WO | WO 00/35346 | 6/2000 |
| WO | WO 03/002054 | 1/2003 |
| WO | WO 03/002967 | 1/2003 |

OTHER PUBLICATIONS

Durfee, W.K., "Preliminary Design and Simulation of a Pneumatic, Stored-Energy, Hybrid Orthosis for Gait Restoration," Proceedings of IMECE04, 2004 ASME International Mechanical Engineering Congress, Nov. 13-20, 2004, [online] [Retrieved on Oct. 9, 2006] Retrieved from the Internet<URL: http://www.me.umn.edu/~wkdurfee/publications/IMECE2004-60075.pdf >.

International Search Report and Written Opinion, PCT/US06/11727, Nov. 9, 2006, 9 pages Isaacs, P.M. et al., "Controlling Dynamic Simulation with Kinematic Constraints, Behavior Functions, and Inverse Dynamics," Computer Graphics, Jul. 1987, pp. 215-224, vol. 21, No. 4.

Madigan, R.R., "Ankle-Foot Orthoses (AFO's) in Spastic Cerebral Palsy," Fillauer LLC, [online] [Retrieved on Oct. 9, 2006] Retrieved from the Internet<URL:http://www.fillauer.com/education/Ed_afo.html#dynamic>.

Pratt, G.A. et al., "Active Orthotics for Helping the Neuromuscularly Impaired to Walk," [online] [Retrieved on Oct. 9, 2006] Retrieved from the Internet<URL:http://www.vcl.uh.edu/~rcv03/materials/grant/9733740.1064791086.pdf>.

"Regenerative Foot Braking," [online] [Retrieved on Oct. 9, 2006] Retrieved from the Internet<URL: http://www.halfbakery.com/idea/regenerative_20foot_20braking#1069693200>.

"Sensorless Fet Element DC Motor Driver," [online] [Retrieved on Oct. 9, 2006] Retrieved from the Internet<URL:http://robotx.sourceforge.net/bridge/bridge.shtml>.

Trost, F.J., "Energy-Storing Feet," JACPOC, 1989, vol. 24, No. 4, [online] [Retrieved on Oct. 9, 2006] Retrieved from the Internet<URL:http://jacpoc.oandp.com/library/1989_04_082.asp>.

PCT International Search Report and Written Opinion, PCT/US06/14069, Aug. 31, 2007, 8 pages.

PCT International Search Report and Written Opinion, PCT/US06/01343, Aug. 15, 2007, 8 pages.

Asensio, J., et al., "A Kinematic and Dynamic Model-Based Motion Controller for Mobile Robots," IFAC, 2002.

Wu, G., et al., "The Study of Kinematic Transient in Locomotion Using the Integrated Kinematic Sensor," IEEE, Sep. 1996, pp. 193-200, vol. 4, No. 3.

PCT International Search Report and Written Opinion, PCT/US06/01116, Jan. 17, 2008.

PCT International Search Report and Written Opinion, PCT/US06/01250, May 16, 2008.

Supplementary European Search Report, EP 06748964, Mar. 14, 2008.

Supplementary European Search Report, EP 06750178, Mar. 14, 2008.

Agarwal, S.K. et al., "Theory and Design of an Orthotic Device for Full or Partial Gravity-Balancing of a Human Leg During Motion," IEEE Transactions on Neural Systems and Rehabilitation Engineering, Jun. 2004, vol. 12, No. 2.

Akhlaghi, F. et al., "In-shoe Biaxial Shear Force Measurement: the Kent Shear System," Medical & Biological Engineering & Computing, Jul. 1996, vol. 34, pp. 315-317.

Anderson, Frank C., "Static and Dynamic Optimization Solutions for Gait are Practically Equivalent", Journal of Biomechancis, 2001, vol. 34, pp. 153-161.

Anderson, F. et al., "Dynamic Optimization of Human Walking," *Journal of Biomechanical Engineering*, Oct. 2001, vol. 123, pp. 381-390.

Anderssen, R. et al., "Numerical Differentiation Procedures for Non-Exact Data," Numererische Mathematik, 1974, vol. 22, pp. 157-182.

Atkeson, C.G., "Learning Arm Kinematics and Dynamics", Annual Reviews, Inc., 1989, vol. 12, pp. 157-183.

Baruh, H., Analytical *Dynamics*, Chapter 7, Rigid Body Kinematics, McGraw-Hill, 1999, pp. 355-371.

Blaya, J., "Force-Controllable Ankle Foot Orthosis (AFO) to Assist Drop Foot Gait," Feb. 2003, web.mit.edu/jblaya/www/MSthesis_final.pdf.

Bronzino, J.D., ed., "The Biomedical Engineering Handbook", IEEE Press, $2^{nd}$ Ed. vol. 2, 2000, Chapter 142, pp. 1-17.

Burdea, G. et al., "Virtual Reality Technology", 1994, pp. 33-37, John Wiley and Sons, Inc.

Busby, H.R. et al., "Numerical Experiments With a New Differentiation Filter," Transactions of the ASME—Journal of Biomechanical Engineering, Nov. 1985, vol. 107, pp. 293-299.

Chao, E.Y. et al., "Application of Optimization Principles in Determining the Applied Moments in Human Leg Joints During Gait," J. Biomechanics, 1973, vol. 6, pp. 497-510, Pergamon Press, Great Britain.

Craig, J.J., "Nonlinear Control of Manipulators," Introduction to Robotics Mechanics and Control, $2^{nd}$. Ed., 1989, Chapter 10, pp. 333-361.

Crowninshield, R.D. et al., "A Physiologically Based Criterion Of Muscle Force Prediction In Locomotion," *Journal of Biomechanics*, vol. 14, No. 11, 1981, pp. 793-801.

Cullum, J., "Numerical Differentiation and Regularization," SIAM J. Numer. Anal., Jun. 1971, vol. 8, No. 2, pp. 254-265.

Dariush, B. et al., "Multi-Modal Analysis of Human Motion From External Measurements," Transactions of the ASME, Jun. 2001, vol. 123, pp. 272-278.

Dariush, B. "A Novel Algorithm For Generating A Forward Dynamics Solution To The Traditional Inverse Dynamics Problem," In $4^{th}$ World Congress of Biomechanics, Calgary, Canada, 2002.

Dariush, B., "A Forward Dynamics Solutions To Multi-Modal Inverse Dynamics Problems," In *International Society of Biomechanics, XIXth Congress*, Dunedin, NZ, 2003.

Dariush, B., "A Well-Posed, Embedded Constraint Representation of Joint Moments From Kinesiological Measurements," Journal of Biomechanical Engineering, Aug. 2000, vol. 122, pp. 437-445.

Delp, S. et al., "A Computational Framework for Simulating and Analyzing Human and Animal Movement," *IEEE Computing in Science and Engineering*, vol. 2, No. 5, 2000, pp. 46-55.

Dohrmann, C.R. et al., "Smoothing Noisy Data Using Dynamic Programming and Generalized Cross-Validation" Transactions of the ASME—Journal of Biomechanical Engineering, Feb. 1988, vol. 110, pp. 37-41.

Flanagan, R.J., et al., "The Role of Internal Models in Motion Planning and Control: Evidence from Grip Force Adjustments During Movements of Hand-Held Loads", The Journal of Neuroscience, Feb. 15, 1997, vol. 17(4), pp. 1519-1528.

Gagnon, D. et al., "The Influence of Dynamic Factors on Triaxial Net Muscular Moments at the L5/S1 Joint During Asymmetrical Lifting and Lowering", Journal of Biomechanics, vol. 25, pp. 891-901, 1992.

Gagnon, M. et al., "Muscular Mechanical Energy Expenditure as a Process for Detecting Potential Risks in Manual Materials Handling," J. Biomech., Nov. 1991, pp. 191-203, vol. 24, No. 3/4.

Giakas, G. et al., "A Comparison of Automatic Filtering Techniques Applied to Biomechanical Walking Data," J. Biomechanics 1997, vol. 00, No. 00, 4 pages.

Giakas, G. et al., "Optimal Digital Filtering Requires a Different Cut-Off Frequency Strategy for the Determination of the Highe Derivatives," J. Biomechanics, Apr. 1997, vol. 28, No. 00, 5 pages.

Grood, E.S. et al., "A Joint Coordinate System for the Clinical Description of Three Dimensional Motions: Application to the Knee," Journal of Biomechanical Engineering, 1983, pp. 136-144, No. 105.

Gruber, K., et al., "A Comparative Study of Impact Dynamics: Wobbling Mass Model Versus Rigid Body Models", Journal of Biomechanics, 31 (1998), pp. 439-444.

Hatze, H. "The Use of Optimally Regularized Fourier Series for Estimating Higher-Order Derivatives of Noisy Biomechanical Data," J. Biomechanics, 1981, vol. 14, pp. 13-18.

Hayashibara, Y. et al., "Design of a Power Assist System with Consideration of Actuator's Maximum Torque," $4^{th}$ IEEE International Workshop on Robot and Human Communication, RO-MAN'95, Tokyo, Jul. 5-7, 1995, pp. 379-384, [online] Retrieved from the Internet<URL:http://ieeexplore.ieee.org/xpl/abs_free.jsp?arNumber=531990>.

Hemami, H., "A Feedback On-Off Model of Biped Dynamics", IEEE Transactions on Systems, Man, and Cybernetics, Jul. 1980, vol. SMC-10, No. 7, pp. 376-383.

Hemami, H. et al., "Modeling And Control Of Constrained Dynamic Systems With Application To Biped Locomotion In The Frontal Plane," *IEEE Transactions on Automatic Control*, vol. 4, No. 4, Aug. 1979, pp. 526-535.

Hemami, H., "A State Space Model for Interconnected Rigid Bodies," IEEE Trans. on Automatic Control, 1982, pp. 376-382, vol. 27, No. 2.

Hosein, R. et al., "A Study of In-shoe Plantar Shear in Normals," Clinical Biomechanics, 2000, vol. 15, pp. 46-53.

Hungspreugs, P. et al., "Muscle Force Distribution Estimation Using Static Optimization Techniques", Technical Report—Honda R&D Americas.

Jalics, L. et al., "A Control Strategy for Terrain Adaptive Bipedal Locomotion," Autonomous Robots, 1997, pp. 243-257, vol. 4.

Jezernk, S. et al., "Robotic Orthosis Lokomat: A Rehabilitation and Research Tool," Neuromodulation, 2003, pp. 108-115, vol. 6, No. 2.

Kato, H. et al., "The Concept of a Walking Assistance Suit", The Japanese Society of Mechanical Engineers, Aug. 2001.

Kawato, M., "Adapation and Learning in Control of Voluntary Movement by the Central Nervous System", 1989, Advanced Robotics, vol. 3, pp. 229-249.

Kawato, M., et al., "The Cerebellum and VOR/OKR Learning Models", Elsevier Science Publishers Ltd., 1992, vol. 15, No. 11, pp. 445-453.

Kawato, M., "Internal Models for Motor Control and Trajectory Planning," Current Opinion in Neurobiology, 1999, pp. 718-727, No. 9.

Khatib, O., A Unified Approach For Motion And Force Control Of Robot Manipulators: The Operational Space Formulation, *IEEE Journal of Robotics and Automation*, RA-3(1), 1987, pp. 43-53.

Klein, C. A. et al., Review Of Pseudoinverse Control For Use With Kinematically Redundant Manipulators, *IEEE Transactions on Systems, Man, and Cybernetics*, vol. 13, No. 2, 1983, pp. 245-250.

Park, J.H. et al., Biped Robot Walking Using Gravity-Compensated Inverted Pendulum Mode and Computed Torque Control, 1998 IEEE Conference on Robotics and Automation, May 16-20, 1998, pp. 2528-2533, vol. 4, [online] Retrieved from the Internet<URL:http://ieeexplore.ieee.org/xpl/abs_free jsp?arNumber=680985>.

Piazza, S. et al., "Three-Dimensional Dynamic Simulation of Total Knee Replacement Motion During a Step-up Task," *Journal of Biomechanical Engineering*, vol. 123, 2001, pp. 599-606.

Rahman, T. et al., "A Simple Technique to Passively Gravity-Balance Articulated Mechanisms," Journal of Mechanical Design, 1995, pp. 655-658, vol. 117, No. 4.

Runge, C.F. et al., "Estimating Net Joint Torques From Kinesiological Data Using Optimal Linear System Theory," IEEE Transactions on Biomedical Engineering, Dec. 1995, vol. 42, No. 12, pp. 1158-1164.

Shadmehr, R. et al., "Interference in Learning Internal Models of Inverse Dynamics in Humans," Advances in Neural Information Processing Systems, 1995, pp. 1117-1224, Chapter 7.

Shadmehr, R., "Learning Virtual Equilibrium Trajectories for Control of a Robot Arm", Neural Computation, 1990, vol. 2, pp. 436-446.

Simons, W. et al., "Differentiation of Human Motion Data Using Combined Spline and Least Squares Concepts," Journal of Biomechanical Engineering, Transactions of the ASME, Aug. 1991, vol. 113, pp. 348-351.

Thelen, D. et al., "Generating Dynamic Simulations of Movement Using Computed Muscle Control," *Journal of Biomechanics*, 36, 2003, pp. 321-328.

Transmittal of the International Search Report, PCT/US02/20829, Dec. 12, 2002, 4 pages.

"Unsupported Standing with Minimized Ankle Muscle Fatigue," [online] Retrieved from the Internet<URL:http://ieeexplore.ieee.org/iel5/10/29163/01315854.pdf>.

Vaughan, C. L. et al., "Appendix B., Detailed Mathematics Used in GaitLab," *Dynamics of Human Gait*, Second Edition, Kiboho Publishers, Cape Town South Africa, 1999, pp. 83-106.

Vukobratovic, M. et al., *Scientific Fundamentals of Robotics 7: Biped Loco-motion*. Springer-Verlag, 1990, pp. 17-27.

Wells, R. et al., "Internal and Physiological Responses During Concentric and Eccentric Cycle Ergometry," Eur. J. Appl. Physiol., 1986, pp. 291-301, vol. 55.

Winter, D.A., "Biomechanics and Motor Control of Human Movement", $2^{nd}$ Edition, John Wiley & Sons, Inc., pp. 51-74.

Winter, D.A., "Kinetics: Forces and Moments of Force," Biomechanics and Motor Control of Human Movement, $2^{nd}$ Ed., New York, 1990, Chapter 4.

Wittenberg, J., *Dynamics of Systems of Rigid Bodies*, 1977, B.G. Teubner Stuttgart, 1977, p. 29-30.

Wolpert, D.M., et al., "Ocular Limit Cycles Induced by Delayed Retinal Feedback", Experimental Brain Research, 1993, vol. 96, pp. 173-180.

Woltring, H.J., "A Fortran Package for Generalized, Cross Validatory Spline Smoothing and Differentiation," Adv. Eng. Software, 1986, vol. 8, No. 2, pp. 104-107.

Woltring, H.J., "On Optimal Smoothing and Derivative Estimation From Noisy Displacement Data in Biomechanics," Human Movement Science, vol. 4, 1985, pp. 229-245.

Written Opinion, PCT/IB02/04311, Feb. 20, 2003, 2 pages.

Zajac, F.E., "Muscle and Tendon Properties, Models, Scaling, and Application to Biomechancis and Motor Control", 1989, vol. 17, Issue 4, pp. 359-411.

Wyeth, G. F., et al., "Distributed Digital Control of a Robot Arm," Proceedings of the Australian Conference on Robotics and Automation (ACRA 2000), Aug. 30-Sep. 1, 2000, pp. 217-222, [online] [retrieved on Dec. 31, 2006] Retrieved from the Internet: <URL: www.itee.ug.edu.au/~wyeth/Publications/puma.PDF>.

PCT International Search Report and Written Opinion, PCT/US06/22582, Feb. 2, 2007, 8 pages.

PCT International Search Report and Written Opinion, PCT/US05/11908, Mar. 8, 2007, 7 pages.

Bhushan, N., et al., "Computational nature of human adaptive control during learning of reaching movements in force fields," Biological Cybernetics, Jan. 26, 1999, p. 39-60, vol. 81.

Goel, P., The Inverse Kinematics Solution, Closed-Form Dynamics and Simulation of AdeptOne Industrial Robot, IEEE, 1988, pp. 1688-1693.

Hardt, M., et al., "The Role of Motion Dynamics in the Design, Control and Stability of Bipedal and Quadrupedal Robots," RoboCup 2002, International Symposium, Jun. 24-25, 2002, pp. 1-16.

Kuster, M., et al., "Joint load considerations in total knee replacement," The Journal of Bone and Joiny Surgery, Jan. 1997, p. 109-113, vol. 79-B, No. 1.

Notice of Grounds for Rejection—Office Action, Japanese Patent Application No. 2003-508905, May 27, 2008, 9 Pages.

Supplementary European Search Report, European Patent Application No. EP 06750178, Apr. 21, 2008, 6 Pages.

Office Action, Canadian Patent Application No. 2,451,630, Jul. 22, 2008, 2 Pages.

Examination Report, European Patent Application No. EP 06748964, Jul. 22, 2008, 5 Pages.

First Office Action of the State Intellectual Property Office issued by the People's Republic of China, Application No. 200710110254.9, Jan. 16, 2009, 8 Pages.

Notice of Grounds for Rejection Office Action issued by the Japan Patent Office, Application No. 2003-508905, Oct. 14, 2008, 7 Pages.

Notice of Grounds for Rejection Office Action issued by the Japan Patent Office, Application No. 2007-552186, Jan. 6, 2009, 8 Pages.

Office Action received for Canada Patent Application No. 2,451,630, Aug. 28, 2009, 2 pages.

* cited by examiner

ACTIVE CONTROL OF AN ANKLE-FOOT ORTHOSIS

CROSS-REFERENCE TO RELATED APPLICATIONS

This application is a continuation-in-part of U.S. patent application Ser. No. 11/395,654, filed on Mar. 30, 2006, and entitled "An Exoskeleton Controller for a Human-Exoskeleton System," which claims priority under 35 U.S.C 119(e) from U.S. provisional applications No. 60/667,518 filed on Apr. 1, 2005, and No. 60/670,732 filed on Apr. 12, 2005, and which is a continuation-in-part of U.S. patent application Ser. No. 11/038,691 filed on Jan. 19, 2005, Ser. No. 11/038,692 filed on Jan. 19, 2005, and Ser. No. 11/038,978 filed on Jan. 19, 2005, which are all incorporated by reference herein in their entirety. U.S. patent application Ser. No. 11/038,691 filed on Jan. 19, 2005, Ser. No. 11/038,692 filed on Jan. 19, 2005, and Ser. No. 11/038,978 filed on Jan. 19, 2005, are each a continuation-in-part of U.S. patent application Ser. No. 10/151,647 filed on May 16, 2002, which claims priority under 35 U.S.C §119(e) from U.S. provisional application No. 60/301,891 filed on Jun. 29, 2001, and No. 60/353,378 filed on Jan. 31, 2002, which are all incorporated by reference herein in their entirety.

This application is related to a continuation in part of U.S. patent application Ser. No. 11/395,654, filed on Mar. 30, 2006, and entitled "An Exoskeleton Controller for a Human-Exoskeleton System," U.S. provisional application No. 60/667,518 filed on Apr. 1, 2005, U.S. Provisional application No. 60/670,732 filed on Apr. 12, 2005, U.S. patent applications No. 11/038,691 filed on Jan. 19, 2005, No. 11/038,692 filed on Jan. 19, 2005, and No. 11/038,978 filed on Jan. 19, 2005, U.S. patent application Ser. No. 10/151,647 filed on May 16, 2002, and U.S. provisional applications No. 60/301,891 filed on Jun. 29, 2001, and No. 60/353,378 filed on Jan. 31, 2002, which are all incorporated by reference herein in their entirety.

This application is also related to U.S. patent application Ser. No. 10/824,059 filed on Apr. 13, 2004, U.S. patent application Ser. No. 10/655,460 filed on Sep. 5, 2003, U.S. provisional applications No. 60/484,708 filed on Jul. 3, 2003, No. 60/421,964 filed on Oct. 28, 2002, and No. 60/413,024 filed on Sep. 23, 2002, U.S. patent application Ser. No. 10/280,771 filed on Oct. 25, 2002, U.S. provisional application No. 60/330,689 filed on Oct. 29, 2001, and No. 60/333,753 filed on Nov. 29, 2001, which are all incorporated by reference herein in their entirety.

FIELD OF THE INVENTION

The present invention relates to the field of orthotics and more particularly to control of an ankle-foot orthosis.

BACKGROUND OF THE INVENTION

Weakness of the ankle or foot can be a significant factor in mobility impairments such as an abnormal gait pattern. One example of this phenomenon is observed in a condition known as drop-foot. A frequent complication associated with drop-foot is an inability to control the falling of the foot after heel strike, so that it slaps the ground at every step, which is referred to as foot-slap. Another complication associated with drop-foot is an inability for toes to clear the ground during swing phase of gait, which causes individuals with drop-foot to drag their toes on the ground throughout swing. Causes of drop-foot can include severed nerves, stroke, cerebral palsy and multiple sclerosis.

Weakness of ankle or foot muscles can also alter the gait pattern of the elderly. Age related changes in stereotypic movements such as walking patterns have been reported as early as age 60. Some of the age-associated changes in gait include a shortened step length, prolonged stance phase and double support times, and decreased ankle push-off power. Efforts to understand impaired mobility of the elderly have been focused on issues related to body support and forward propulsion.

Changes in patterns of mobility as a consequence of neurological or age related disorders can result in unsafe and energy consuming movement. In the case of drop foot, for example, accidental falls can occur during walking when the person catches their toes on the ground. A lack of balance control is also a major potential cause of falls involving a significant risk of injury. To provide another example, patients often compensate for drop-foot by excessively raising their hip or knee to ensure clearance of the foot off the ground, which is referred to as a steppage gait and which resembles the gait of a high-stepping horse. A steppage gait pattern expends more energy than normal, causing fatigue and making it more difficult and dangerous to walk.

An ankle-foot orthosis (AFO) is an orthopedic device that can provide support, stability, or replacement of lost function to the ankle. In North America, there are approximately 100,000 ankle-foot orthoses prescribed for children and adults with neuromuscular disorders such as spina bifida and cerebral palsy. Ankle orthotics can be useful after an acute ankle injury, for rehabilitation, to prevent ankle re-injury, for fall prevention in the elderly, and for chronically unstable ankles.

In a recently developed ankle-foot orthosis, the impedance of the orthotic joint was modulated throughout the walking cycle to treat drop foot gait. See Joaquin A. Blaya, Force-controllable ankle foot orthosis (AFO) to assist drop foot gait, Master's thesis, Massachusetts Institute of Technology, 2003, which is incorporated by reference herein in its entirety. It was found that actively adjusting joint impedance reduces the occurrence of slap foot, allows greater powered plantar flexion, and provides for greater biological realism in swing phase ankle dynamics.

Control of a human-exoskeleton system such as an ankle-foot orthosis presents significant challenges due to the complexity of the central nervous system (CNS) control and the interface between voluntary control and external artificial control. When humans interact with an external force field such as an exoskeleton, the central nervous system needs to learn an internal model of the force field and interaction with the force field. See R. Shadmehr, T. Brashers-Krug, and F. Mussa-Ivaldi, Interference in learning internal models of inverse dynamics in humans, in G. Tesauro, D. S. Touretsky, and T. K. Leen, eds., Advances in Neural Information Processing Systems, chapter 7, pages 1117-1224, MIT Press, 1995, which is incorporated by reference herein in its entirety. Therefore, a major challenge in the design and use of ankle-foot orthoses for daily activities relates to the coupled control of a human-exoskeleton system.

Another challenge to controlling an ankle-foot orthoses is that an expected trajectory is not available to the controller because the intended human motion cannot be predicted in advance by an exoskeleton controller. Human motion generally takes place in a dynamic environment and forces that will act on a body are also unpredictable. The inability to predict the intended motion in addition to interaction with uncertain dynamic environments creates a need for online or real-time control of an ankle-foot orthoses.

Conventional techniques for human-exoskeleton control tend to rely on unreliable calculation of first and second order time derivatives of noisy generalized coordinates. Conventional exoskeleton controllers are also susceptible to uncertainties in measurement of body parameters such as body segment mass, center of mass, and length. For example, conventional inverse dynamics control requires precise dynamic models because it is sensitive to parametric uncertainties. Further, coupled control of a human-exoskeleton system may lead to mechanical and metabolic inefficiencies if the assist controller is not properly designed.

For an ankle-foot orthosis, there is a need for practical and effective control strategies that can address mobility impairments such as abnormal gait patterns without the errors caused by calculation of higher order derivatives of noisy kinematic data. There is a need for ankle-foot orthosis controllers that are compatible with complex voluntary control performed by the central nervous system and that are capable of energy efficient, real-time control.

SUMMARY OF THE INVENTION

One embodiment of the present invention provides a computer based method of controlling a human-exoskeleton system comprising an ankle-foot orthosis at an ankle joint. The method comprises receiving system parameters for the human-exoskeleton system, receiving generalized coordinates such as an orientation of a foot connected to the ankle joint, and determining a joint torque for controlling the ankle-foot orthosis to compensate for one or more components of forces acting on the foot. Forces selected for compensation can include gravitational forces as well as external forces such as ground reaction forces. According to one embodiment of the present invention, the ankle-foot orthosis is an active ankle-foot orthosis.

According to one embodiment of the present invention, the control torque required to generate motion is relegated to muscles actuators that are activated by voluntary commands from the central nervous system, thereby mitigating the amount of interference between voluntary control and assist control and allowing humans to quickly adapt to an ankle-foot orthosis. One embodiment of the present invention advantageously provides for efficient, real-time control of an ankle-foot orthosis without the errors caused by calculation of higher order derivatives of noisy kinematic data.

One embodiment of the present invention determines an ankle-joint torque to compensate for sheer and/or vertical components of ground reaction forces acting on the foot. Another embodiment of the present invention determines an ankle-joint torque to compensate for a dynamic component of a vertical ground reaction force acting on the foot. Yet another embodiment of the present invention determines an ankle joint torque to compensate for vertical components of forces acting on the foot. According to one embodiment of the present invention, linear or angular velocities or accelerations associated with the foot can be set to zero while determining the ankle-joint torque based on an inverse dynamics procedure.

One embodiment of the present invention determines an ankle joint torque to provide compensation for forces acting on the foot about an axis or rotation of an ankle-foot orthosis. Another embodiment of the present invention determines an ankle joint torque for partial compensation of forces acting on the foot for one or more degrees of freedom.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

DETAILED DESCRIPTION OF THE PREFERRED EMBODIMENTS

Figure 1:
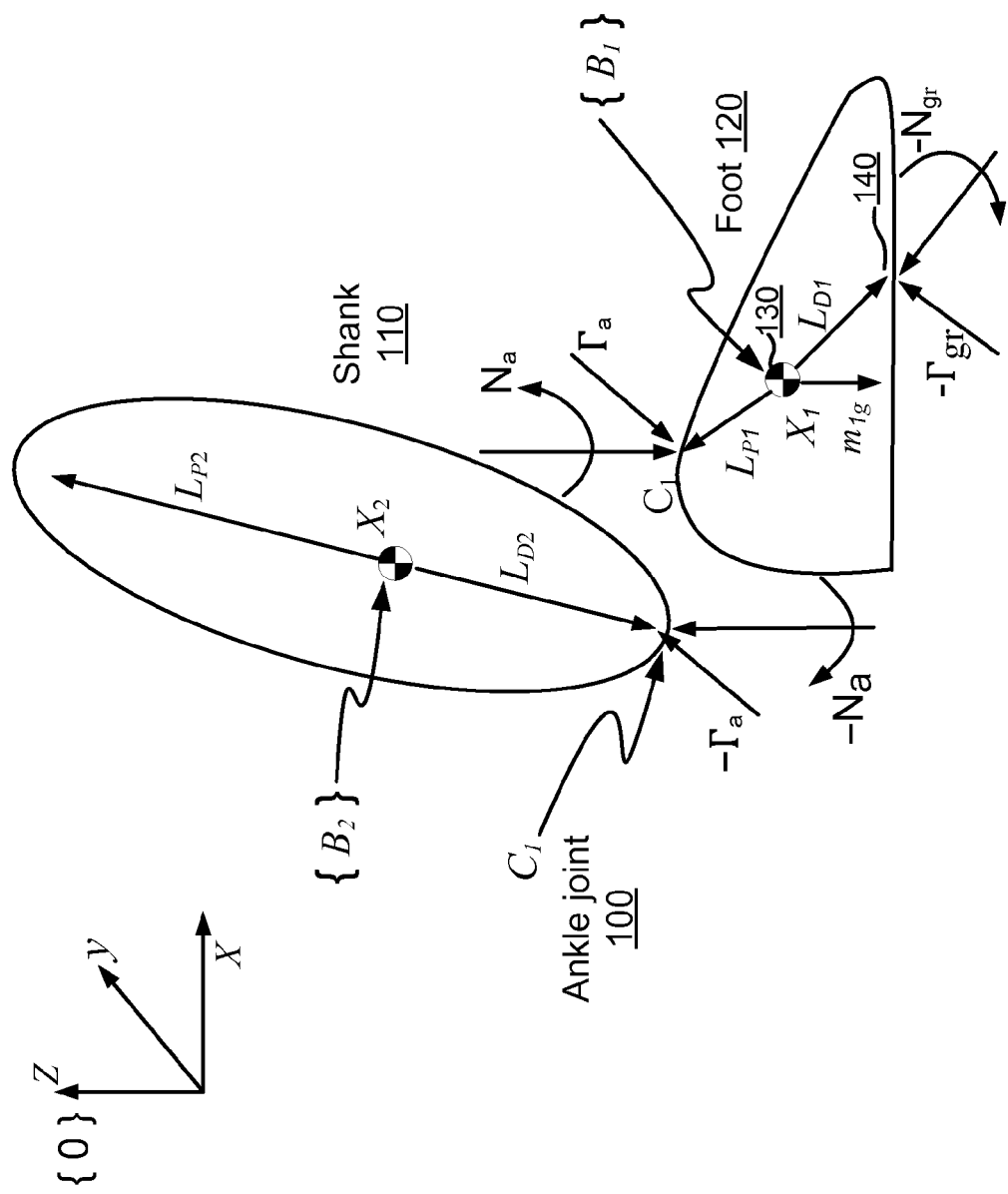
FIG. 1 is a free body diagram of forces and moments acting on a foot-shank system according to one embodiment of the present invention.

A preferred embodiment of the present invention is now described with reference to the figures where like reference numbers indicate identical or functionally similar elements. Also in the figures, the left most digits of each reference number corresponds to the figure in which the reference number is first used.

Reference in the specification to "one embodiment" or to "an embodiment" means that a particular feature, structure, or characteristic described in connection with the embodiments is included in at least one embodiment of the invention. The appearances of the phrase "in one embodiment" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantifies within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

In addition, the language used in the specification has been principally selected for readability and instructional purposes, and may not have been selected to delineate or circumscribe the inventive subject matter. Accordingly, the disclosure of the present invention is intended to be illustrative, but not limiting, of the scope of the invention, which is set forth in the following claims.

Control of an ankle-foot orthosis according to one embodiment of the present invention can be utilized to counteract the muscle weakness in the foot or ankle and to aid several functions in ambulation, including control of dorsiflexion and plantar-flexion in both the stance and swing phases of gait. By actively adjusting joint impedance through control of an ankle-foot orthosis, one embodiment of the present invention reduces the occurrence of slap foot, allows for improved powered plantar flexion, and provides for greater biological realism in swing phase ankle dynamics. One embodiment of the present invention provides for an active or powered ankle-foot orthosis.

Control of an ankle-foot orthosis can be relegated into two control subsystems: exoskeleton control and Central Nervous System (CNS) control. See U.S. patent application Ser. No. 10/824,059 filed on Apr. 13, 2004, which is incorporated by reference herein in its entirety; see U.S. patent application Ser. No. 11/395,654, filed on Mar. 30, 2006, and entitled "An Exoskeleton Controller for a Human-Exoskeleton System," which is incorporated by reference herein in its entirety. According to one embodiment of the present invention, the exoskeleton control subsystem can be responsible for determining an ankle joint torque required to partially or completely compensate for vertical components of one or more forces acting on the foot, such as gravitational or external forces. According to one embodiment, the exoskeleton control subsystem can be responsible for determining an ankle joint torque required to partially or completely compensate for ground reaction forces acting on the foot. One embodiment of the present invention provides a weight bearing control strategy based on partial or complete gravity compensation for control of powered ankle-foot orthosis, wherein the gravity compensation control accounts for the potential energy of the system and is responsible for compensating for torques due to gravity. According to one embodiment, the ankle joint torque computed by the exoskeleton control system does not account for generating the control commands to produce the intended motion, which can be relegated to the CNS.

Compensation for gravity forces is important because a large component of muscle torques required to execute many tasks is due to compensation for gravitational loads due to the body segments. For example, the ankle joint muscles may need to accommodate nearly the entire body weight in order to keep balance. In additional to gravity forces due to body segments, a human-exoskeleton system is subjected to external forces such as interaction forces arising from human-exoskeleton interaction, contact forces with the environment, ground reaction forces, applied forces, and gravitational forces due to loads (e.g. a backpack) external to the human body. External forces or their components are often known or may be reliably measured. For example, the vertical component of a ground reaction force is a type of external constraint force that can be reliably measured using in-shoe pressure/force sensors.

According to one embodiment of the present invention, an ankle-foot orthosis controller that performs partial compensation for one or more forces leaves the CNS control to execute commands that produce the muscle forces required to compensate for the remaining static and the kinetic components of motion. For example, the ankle-foot orthosis can compensate for gravitational forces and/or ground reaction forces. The relegation of control according to one embodiment of the present invention leaves the responsibility of motion execution, also referred to as motion generation or control of motion, to the CNS/musculoskeletal system while the ankle-foot orthosis controllers and actuators contribute, at least in part, to maintaining static equilibrium. Such a partitioning into kinetic energy and partial potential energy components has important implications in motor learning. When humans interact with an external force field such as an exoskeleton, the central nervous system needs to learn an internal model of the force field and the interaction with that force field. See R. Shadmehr, T. Brashers-Krug, and F. Mussa-Ivaldi, Interference in learning internal models of inverse dynamics in humans, in G. Tesauro, D. S. Touretsky, and T. K. Leen, editors, Advances in Neural Information Processing Systems, chapter 7, pp. 1117-1224, MIT Press, 1995, which is incorporated by reference herein in its entirety. By partitioning the human and exoskeleton control to the corresponding kinetic and potential energy, one embodiment of the present invention mitigates the amount of interference between voluntary control and assist control, and minimizing such interference plays an important role in how quickly humans can adapt to interaction with the ankle-foot orthosis. Accordingly, one embodiment of the present invention provides a clear partition between natural voluntary control by the CNS and artificial assist by the ankle-foot orthosis controller.

One embodiment of the present invention can effectively address problems associated with unmodeled dynamics, modeling uncertainties and measurement errors. One embodiment of the present invention does not require sophisticated sensory inputs because readily-obtained information, for example the mass of the foot, is sufficient to determine ankle joint torque for control of an ankle-foot orthosis. Further, since joint torques can be determined as a function of joint positions and orientations and do not contain velocity or acceleration terms, one embodiment of the present invention is not sensitive to noise amplification from numerical differentiation of noisy kinematic variables. In addition, one embodiment of the present invention utilizes ground reaction forces as constraints in conjunction with recursive computations to confine determination of the joint torque to the foot-ankle system. By confining determination of the joint torque to the foot-ankle system, one embodiment of the present invention obviates modeling the entire body and therefore reduces the effects of unmodeled dynamics, parametric uncertainties, and noise propagation. Moreover, one embodiment of the present invention has limited sensitivity to parametric uncertainties as compared to inverse dynamics control because this embodiment uses the mass of the foot as the only model parameter.

Human gait is efficient due to the passive transfer of potential to kinetic energy from gravitational forces. Such efficiency is observed at the hip joint, where the pendulum like motion of the lower legs during swing requires little energy from the hip muscles. The transfer of kinetic energy to potential energy plays a less significant role at the ankle joint. In fact, a significant role of the ankle muscles is to overcome the destabilizing effect of gravity and to assist human gait during toe-off. Accordingly, one embodiment of the present invention provides an effective control strategy for an ankle-foot orthosis by partially or completely compensating for gravitational forces acting on the foot.

Foot-Shank System

FIG. 1 is a free body diagram of forces and moments acting on a foot-shank system according to one embodiment of the present invention. FIG. 1 illustrates the description of relevant frames, position vectors, and forces and moments acting on a foot-shank system comprising an ankle joint 100 connecting a shank 110 and a foot 120 according to one embodiment of the present invention. The motion of the foot 120 can be described by two coordinate systems, a space-fixed or inertial coordinate system (ICS), and a moving body-fixed coordinate system ($B_1$CS) which is rigidly fixed to foot 120 and participates in its motion. The frame description for the ICS and $B_1$CS is denoted by $\{O\}$ and $\{B_1\}$, respectively.

The origin of frame $\{B_1\}$ represents the position of the center of mass 130 of foot 120. The position of the center of mass 130 of foot 120 relative to frame $\{O\}$ is described by the vector $X_1$. The ankle joint center 100 is described by the vector $C_1$ with respect to frame $\{O\}$. The position vectors in frame $\{O\}$ from foot center of mass 130 to foot center of pressure 140 is described by $L_{D1}$. The position vector in frame $\{O\}$ from foot center of mass 130 to ankle joint 100 is described by $L_{P1}$. The position vector in frame $\{O\}$ from shank center of mass $X_2$ to ankle joint 100 is described by $L_{D2}$, while $L_{P2}$ describes the position vector in frame $\{O\}$ from shank center of mass to the knee joint.

The totality of all torques acting at a joint, including torques generated from the voluntary contraction of muscle actuators and torques generated from artificial actuators in an exoskeleton system is referred to as the net joint torque. The force due to gravity acting at foot center of mass 130 is denoted by $m_1 g$, where $m_1$ is the mass of foot 120 and g is a 3×1 vector representing the acceleration due to gravity. The joint reaction force exerted on foot 120 by shank 110 at ankle 100 is denoted by $\Gamma_a$ with respect to frame $\{O\}$, and the ground reaction force acting on foot 120 is denoted by $\Gamma_{gr}$ with respect to frame $\{O\}$. The three dimensional moment exerted on foot 120 by shank 110 at ankle joint 100 is described by $^1N_a$ with respect to frame $\{B_1\}$. The ground reaction moment acting on foot 120 is denoted by $^1N_{gr}$ with respect to frame $\{B_1\}$. According to one embodiment of the present invention, the ground reaction force $\Gamma_{gr}$ and ground reaction moment $^1N_{gr}$ can be considered to be acting at foot center of pressure 140. Vectors are written with a leading superscript, which indicates the coordinate system to which the vector is referenced, and the absence of a leading superscript indicates a vector with respect to the default frame $\{O\}$. For example, $^1N_a$ represents a vector whose components have numerical values about the axis of frame $\{B_1\}$.

Description of Rotation Transforms

The orientation of frame $\{B_1\}$ relative to frame $\{O\}$ is achieved through orthogonal matrix $^oR_1$. The rotation matrix represents three consecutive rotations using Euler angles $\Theta=[\phi, \theta, \psi]^T$. We can associate the transformation order in matrix $^oR_1$ with the 3-1-3 (or z-x-z) Euler angle sequence. Each rotation is performed about an axis of the moving reference frame. The explicit expression for the rotation matrix is given by equation 1, where the notations c and s represent sin( ) and cos( ), respectively.

$$^oR_1 = \begin{bmatrix} c\phi\ c\psi - s\phi\ c\theta\ s\psi & -c\phi\ s\psi - s\phi\ c\theta\ c\psi & s\phi\ s\theta \\ s\phi\ c\psi + c\phi\ c\theta\ s\psi & -s\phi\ s\psi + c\phi\ c\theta\ c\psi & -c\phi\ s\theta \\ s\theta\ s\psi & s\theta\ c\psi & c\theta \end{bmatrix} \quad (1)$$

The inverse transformation from frame $\{O\}$ to frame $\{B_1\}$ is given by equation 2.

$$^1R_o = {^oR_1}^{-1} = {^oR_1}^T \quad (2)$$

The Euler angles and their derivatives in terms of the angular velocity $W=[w_x, w_y, w_z]^T$ along the body fixed axes is given by equation 3. See H. Baruh, Analytical Dynamics, WCB/McGraw-Hill, 1999; J. Wittenburg, Dynamics of Systems of Rigid Bodies, B. G. Teubner Stuttgart, 1977, which are all incorporated by reference herein in their entirety.

$$\dot{\Theta} = H^{-1}W \quad (3)$$

$H^{-1}$ is defined in additional detail by equation 4 below.

$$H^{-1} = \begin{bmatrix} s\psi/s\phi & c\psi/s\phi & 0 \\ c\psi & -s\psi & 0 \\ s\psi\, c\theta/s\theta & -c\psi\, c\theta/s\theta & 1 \end{bmatrix} \quad (4)$$

The inverse transform is given by equation 5.

$$W = H\dot{\Theta} \quad (5)$$

H is defined in additional detail by equation 6.

$$H = \begin{bmatrix} s\theta\, s\psi & c\psi & 0 \\ s\theta\, c\psi & -s\psi & 0 \\ c\theta & 0 & 1 \end{bmatrix} \quad (6)$$

Figure 2:
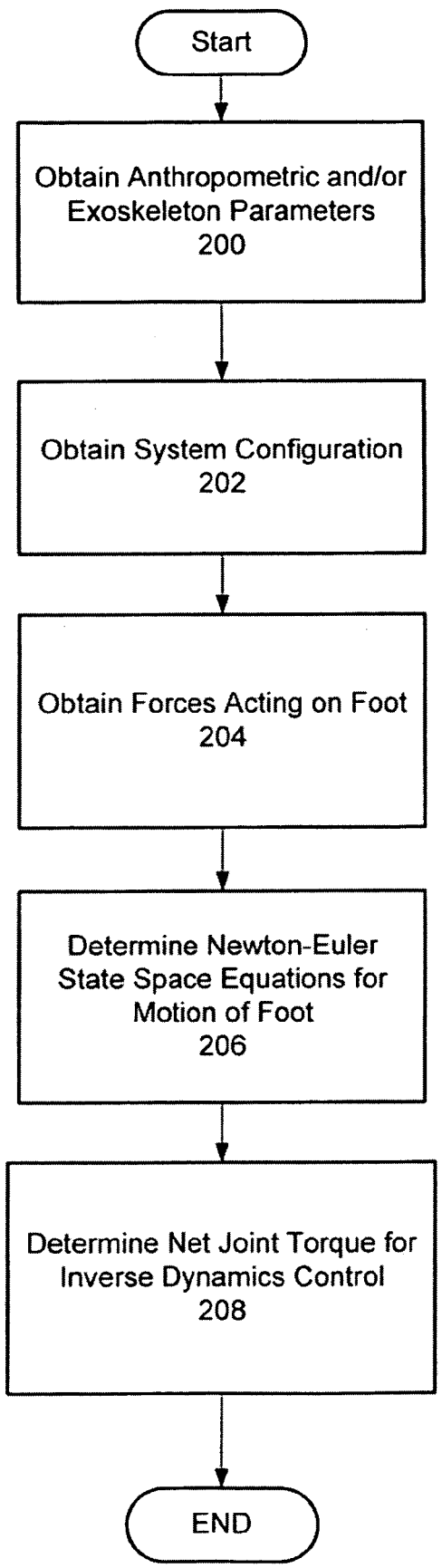
FIG. 2 is a flowchart illustrating a method of determining ankle joint torque by analyzing forces and moments acting on the foot according to one embodiment of the present invention.

Determining Ankle Joint Torque by Analyzing
Forces and Moments Acting on the Foot FIG. 2 is a flowchart illustrating a method of determining ankle joint torque by analyzing forces and moments acting on foot 120 according to one embodiment of the present invention. The method obtains 200 anthropometric and exoskeleton parameters, also referred to as system parameters, such as the mass of foot 120, the location of foot center of mass 130, and location of the ankle joint 100 with respect to the foot center of mass 130. The current system configuration can be obtained 202 by measuring or estimating generalized coordinates of the human-exoskeleton system. For example, the foot center of pressure 140 can be obtained 202 at each instant in time using force sensors attached to foot 120, which can be used to perform online or real time control of an ankle-foot orthosis. System configuration information can also include orientation of foot 120, for example the current ankle angle. Forces acting on foot 120, such as one or more components of a ground reaction force, can be obtained 204 by measuring or estimating the forces at each instant in time. For example, ground reaction forces acting on foot 120 can be measured using force plates or sensors, such as in-shoe force sensors. Note that some of the inputs described above, such as the location of foot center of pressure 140 and ground reaction forces acting on foot 120 may not be needed to determine an ankle joint torque when foot 120 is not in contact with the ground.

One embodiment of the present invention determines 206 Newton-Euler equations to analyze forces and moments acting on foot 120. As explained above with reference to FIG. 1, the notation of leading superscript is used to indicate the coordinate system to which a joint moment is referenced. The Newton-Euler state space equations describing the motion of foot 120 about its center of mass 130 are shown in equations 7-9. See H. Hemami, A state space model for interconnected rigid bodies, IEEE Trans. on Automatic Control, 27(2):376-382, 1982, which is incorporated by reference herein in its entirety.

$$m_1\ddot{X}_1 = \Gamma_{gr} - \Gamma_a - m_1 g \quad (7)$$

$$\dot{\Theta}_1 = H_1^{-1} W_1 \quad (8)$$

$$I_1\dot{W}_1 = -f(W_1) + {}^1N_{gr} - {}^1N_a + {}^1R_o(L_{P1} \times \Gamma_a) \quad (9)$$

In equations 7-9, $I_1$ is the inertia tensor of foot 120 in frame $\{B_1\}$ and $f(W) = W \times IW$ is known as the "gyroscopic torque".

According to one embodiment of the present invention, rotational equation 9 can be simplified by selecting the body fixed axis as the principle axis. By doing so, product of inertias vanish and the inertia tensor becomes a diagonal matrix, $I = \text{diag}([I_x, I_y, I_z])$. The gyroscopic torque simplifies to equation 10.

$$f(W) = \begin{bmatrix} (I_z - I_y) w_y w_z \\ (I_x - I_z) w_x w_z \\ (I_y - I_x) w_x w_y \end{bmatrix} \quad (10)$$

According to one embodiment of the present invention, to avoid using cross products in Equation 9, consider the identity in equation 11 for the cross product of arbitrary vectors a and b.

$$a \times b = \tilde{a} b \quad (11)$$

In equation 11, the tilde symbol (~) denotes the skew symmetric matrix representation of a vector. For example, with the vector $L = [l_x\, l_y\, l_z]^T$ one can associate the 3×3 skew symmetric matrix $\tilde{L}$ defined in equation 12.

$$\tilde{L} = \begin{bmatrix} 0 & -l_z & l_y \\ l_z & 0 & -l_x \\ -l_y & l_x & 0 \end{bmatrix} \quad (12)$$

Using the notations described above, equations 7-9 can be rewritten as equations 13-15.

$$m_1\ddot{X}_1 = \Gamma_{gr} - \Gamma_a - m_1 g \quad (13)$$

$$\dot{\Theta}_1 = H_1^{-1} W_1 \quad (14)$$

$$I_1 \dot{W}_1 = -f(W_1) + {}^1N_{gr} - {}^1N_a + {}^1R_o \tilde{L}_{D1} \Gamma_{gr} - {}^1R_o \tilde{L}_{P1} \Gamma_a \quad (15)$$

According to one embodiment of the present invention, if the ground reaction force $\Gamma_{gr}$ and ground reaction moment ${}^1N_{gr}$ are available, Equations 13-15 can be used to calculate the joint reaction moment ${}^1N_a$ at the ankle, which can be compensated by an ankle-foot orthosis.

One embodiment of the present invention determines the ankle-joint torque about one or more particular axes of rotation. The ankle torque couple ${}^oN_a$ is a three dimensional vector expressed in the global reference frame. For control of an AFO, one embodiment of the present invention describes the ankle joint moment about physically and anatomically meaningful rotation axes. The flexion/extension, internal/external, and eversion/inversion are three axes that can be used in clinical description of ankle motion. The torque about the flexion/extension axis is prominent in absorption and generation of power in human activities such as gait. According to one embodiment of the present invention, the component of ${}^oN_a$ about a specified axis is determined by taking the dot product of ${}^oN_a$ and a unit vector in the direction of the axis of rotation. Let $\hat{s}$ define a unit vector in the direction of the flexion/extension axis with respect to frame $\{O\}$. According to one embodiment of the present invention, the net joint torque about the flexion/extension axis is a scalar quantity given by equation 16.

$$M_{flx/ext} = {}^oN_a^T \hat{s} \quad (16)$$

Inverse dynamics control is one method for controlling the ankle joint. One embodiment of the present invention determines 208 the net joint torque about a particular axis of rotation, for example the flexion/extension axis, for inverse dynamics control. As shown in equation 17, equation 16 represents the net joint torque about the $\hat{s}$ axis, or the control law for inverse dynamics control, which can be used for active control of an ankle-foot orthosis according to one embodiment of the present invention. In the absence of noise, with accurate measurements and an accurate biomechanical model, the control law in equation 17 allows the total power required from the muscles during flexion/extension to be provided by the ankle-foot orthosis.

$$U_{NJT} = M_{flx/ext} \quad (17)$$

Figure 3:
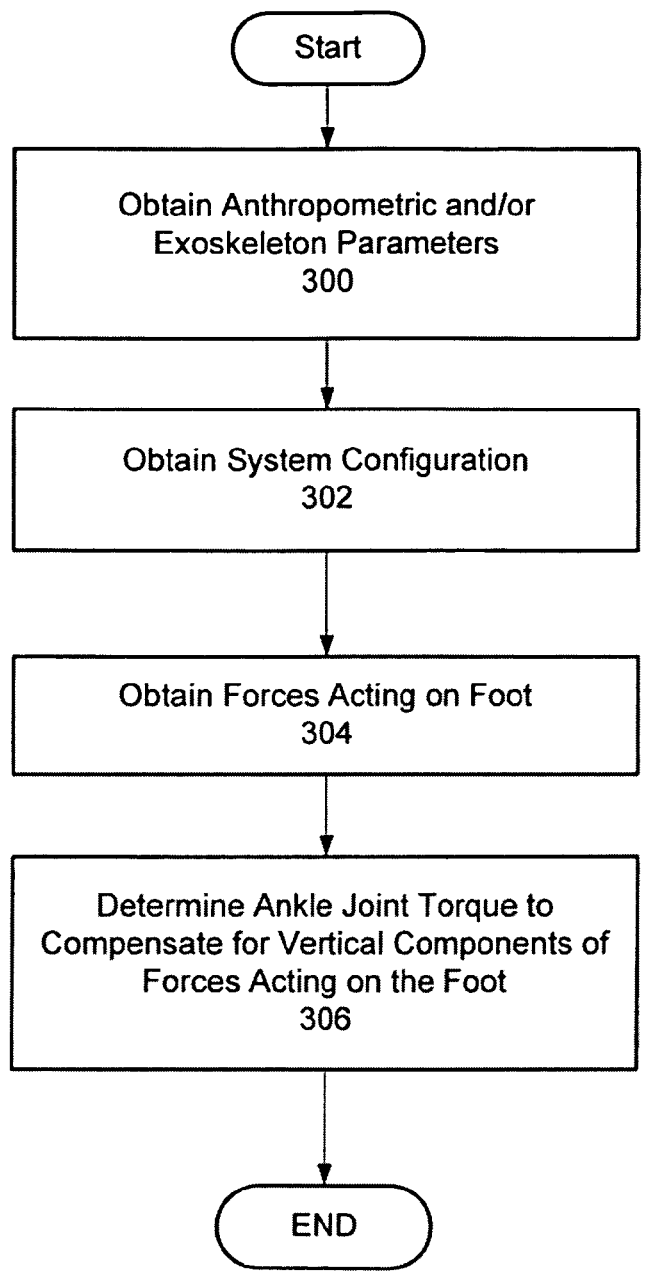
FIG. 3 is a flowchart illustrating a method of determining an ankle joint torque to compensate for vertical components of forces acting on the foot according to one embodiment of the present invention.

Determining Ankle Joint Torque to Compensate for Vertical Components of Forces Acting on the Foot FIG. 3 is a flowchart illustrating a method of determining an ankle joint torque to compensate for vertical components of forces acting on foot 120 according to one embodiment of the present invention. The method obtains 300 one or more anthropometric and exoskeleton parameters, also referred to as system parameters, such as the mass of foot 120, the location of foot center of mass 130, and location of the ankle joint 100 with respect to the foot center of mass 130. The mass of foot 120 can also include the mass of any attachments to foot 120, such as a shoe. The current system configuration can be obtained 302 by measuring or estimating generalized coordinates of the human-exoskeleton system. For example, the rotation matrix $^1R_o$ representing the orientation of foot 120 can be obtained 302 at each instant in time, which can be used to perform online or real time control of an ankle-foot orthosis. System configuration information can also include the location of foot center of pressure 140, which can also be obtained at each instant in time using force sensors attached to foot 120, and which can be used for online control of an ankle-foot orthosis. Forces acting on foot 120, such as one or more components of a ground reaction force, can be obtained 304 by measuring or estimating the forces. For example, ground reaction forces acting on foot 120 can be measured at each instant in time using sensors or force plates. Note that some of the inputs described above, such as the location of foot center of pressure 140 and ground reaction forces acting on foot 120 may not be needed to determine an ankle joint torque when foot 120 is not in contact with the ground.

According to one embodiment of the present invention, motion execution is relegated to voluntary commands from the CNS, wherein the CNS can be assigned the role of issuing the commands to generate a desired motion. These commands are in the form of neural signals that activate the muscles to generate muscle torques required to produce a desired motion.

One embodiment of the present invention determines 306 an ankle joint torque to compensate for vertical components of forces acting on foot 120. For example, to perform gravity compensation control at the ankle 100, we may consider only those forces in the direction of the gravitation force (z-direction) as shown in equations 18-19. According to a further embodiment, the ground reaction moment, velocity and acceleration terms in equations 13-15 can also be set to zero, as shown in equations 20-24. For example, a linear velocity or acceleration associated with foot 120 can be set to zero when determining the ankle joint torque. To provide another example, an angular velocity or acceleration associated with foot 120 can be set to zero when determining the ankle joint torque. According to one embodiment of the present invention, the ankle joint torque determined in step 306 can be used to control an ankle-foot orthosis.

$$\Gamma_{gr}(x) = 0 \quad (18)$$

$$\Gamma_{gr}(y) = 0 \quad (19)$$

$$^1N_{gr} = 0 \quad (20)$$

$$\dot{\Theta}_1 = 0 \quad (21)$$

$$W_1 = 0 \quad (22)$$

$$\dot{W}_1 = 0 \quad (23)$$

$$\ddot{X}_1 = 0 \quad (24)$$

According to one embodiment of the present invention, based on equations 13-15 and the constraints in equations 18-24, an ankle joint torque to compensate for the vertical components of forces acting on foot 120 can be determined 306 using equation 25. The vertical component of the ground reaction force can be obtained, for example, by measurement or estimation.

$$^1N_{AJT} = {}^1R_o \tilde{L}_{D1} \Gamma_{gr}(z) - {}^1R_o \tilde{L}_{P1}(\Gamma_{gr}(z) - m_1 g) \quad (25)$$

According to one embodiment of the present invention, equation 25 can be written as equation 27 by using the simplification in equation 26.

$$L = L_{D1} - L_{P1} \quad (26)$$

$$^1N_{AJT} = {}^1R_o \{\tilde{L} \Gamma_{gr}(z) + \tilde{L}_{P1} m_1 g\} \quad (27)$$

If the segment lengths are expressed in the body-fixed coordinate system, for example in online control of an ankle-foot orthosis, equation 27 can be written as equation 28. Equation 28 can be used to determine 306 an ankle joint torque to compensate for the vertical component of the ground reaction force and the gravitational force acting on foot 120 according to one embodiment of the present invention.

$$^1N_{AJT_I} = {}^1\tilde{L} {}^1R_o \Gamma_{gr}(z) + {}^1\tilde{L}_{P1} {}^1R_o m_1 g \quad (28)$$

According to one embodiment, not every degree of freedom is actuated because it is not always necessary to have a motorized actuator at every degree of freedom of the ankle joint 100. Let $^1\hat{S}$ define a unit vector in the direction of an axis of rotation, for example the flexion/extension axis, referred to the foot reference frame. Based on equation 28, the actuator control about an axis of rotation is given by equation 29. According to one embodiment of the present invention, online control of an ankle-foot orthosis can be achieved by using real time Euler angles to obtain the rotation matrix, as shown in equations 1-2 above.

$$U_{AJT_I} = {}^1N_{AJT_I} \cdot {}^1\hat{S} \quad (29)$$

For an actuated degree of freedom, it may not be desirable to generate an assist torque that fully compensates for gravity or ground reaction forces. One embodiment of the present invention determines an ankle joint torque for partial compensation using an assist ratio that actuates a fraction of the total torque at the ankle joint 100. According to one embodiment of the present invention, an ankle joint torque for partial compensation of a degree of freedom can be determined by pre-multiplying equation 29 with an assist ratio a as shown in equation 30. The assist ratio a can have a value between zero and one for partial assist, a value of zero for no assist, and a value of one for full assist of an actuated degree of freedom.

$$\tau_{AJT_I} = a {}^1N_{AJT_I} \cdot {}^1\hat{S} \quad (30)$$

According to one embodiment of the present invention, compensation for the gravitational force due to foot 120 in equation 28 can be ignored, for example if the foot gravitational force is small compared to the vertical component of the ground reaction force. Accordingly, one embodiment of the present invention determines 306 an ankle joint torque that compensates for the vertical component of the ground reaction force, as shown in equation 31.

$${}^1N_{AJT_{II}} = {}^1\tilde{L}^1 R_o \Gamma_{gr}(z) \tag{31}$$

Based on equation 31, the actuator control about an axis of rotation is given by equation 32. According to one embodiment of the present invention, online control of an ankle-foot orthosis can be achieved by using real time Euler angles to obtain the rotation matrix, as shown in equations 1-2 above.

$$U_{AJT_{II}} = {}^1N_{AJT_{II}} \cdot {}^1\hat{S} \tag{32}$$

According to one embodiment of the present invention, an ankle joint torque for partial compensation of a degree of freedom can be determined by pre-multiplying equation 32 with an assist ratio a as shown in equation 33. The assist ratio a can have a value between zero and one for partial assist, a value of zero for no assist, and a value of one for full assist of an actuated degree of freedom.

$$\tau_{AJT_{II}} = a {}^1N_{AJT_{II}} \cdot {}^1\hat{S} \tag{33}$$

Referring to equations 25-33, according to one embodiment of the present invention a static component of the vertical ground reaction force as well as a dynamic component of the vertical ground reaction force can be used to determine an ankle joint torque. In some instances, for example in the double support phase of motion, the static component may not be readily obtainable. One embodiment of the present invention determines 306 an ankle joint torque that compensates for vertical components of forces acting on foot 120 by using the dynamic component of the vertical ground reaction force in place of the vertical ground reaction force $\Gamma_{gr}(z)$ in equations 25-33. For example, an ankle joint torque that compensates for the dynamic component of the vertical ground reaction force and the gravitational force acting on foot 120 can, be determined using equations 28-30. To provide another example, an ankle joint torque that compensates for the dynamic component of the vertical ground reaction force can be determined using equations 31-33. The dynamic component of the vertical ground reaction force is available, for example, by using force and pressure sensors. One example of a force sensor is an in-shoe force sensor.

Referring to equations 25-33, according to one embodiment of the present invention the ankle joint torque for controlling an ankle-foot orthosis can be determined without the need for online measurement information, for example if the orientation of the foot 120 is known a priori and is identical to the orientation of the foot coordinate system at run-time and/ or if the ground reaction force is constant, known a priori and identical to the ground reaction force at run-time.

Figure 4:
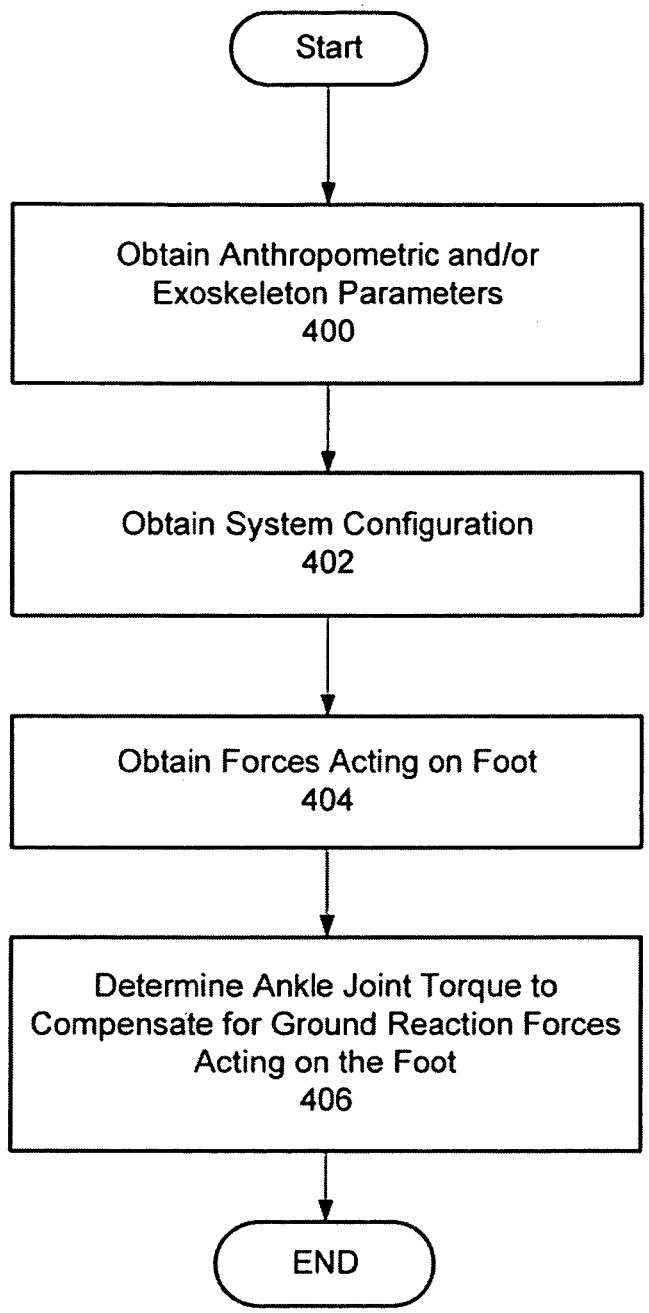
FIG. 4 is a flowchart illustrating a method of determining an ankle joint torque to compensate for ground reaction forces acting on the foot according to one embodiment of the present invention.

Determining Ankle Joint Torque to Compensate for Ground Reaction Forces Acting on the Foot FIG. 4 is a flowchart illustrating a method of determining an ankle joint torque to compensate for ground reaction forces acting on foot 120 according to one embodiment of the present invention. The method obtains 400 one or more anthropometric and exoskeleton parameters, also referred to as system parameters, such as the location of foot center of mass 130 and location of ankle joint 100 with respect to the foot center of mass 130. The current system configuration can be obtained 402 by measuring or estimating generalized coordinates of the human-exoskeleton system. For example, the rotation matrix $^1R_o$ representing the orientation of foot 120 can be obtained 402 at each instant in time, which can be used to perform online or real time control of an ankle-foot orthosis. System configuration information can also include the location of foot center of pressure 140, which can also be obtained at each instant in time using force sensors attached to foot 120, and which can be used for online control of an ankle-foot orthosis. Forces acting on foot 120, such as one or more components of a ground reaction force, can be obtained 404 by measuring or estimating the forces. For example, ground reaction forces acting on foot 120 can be measured at each instant in time using sensors or force plates. Note that some of the inputs described above, such as the location of foot center of pressure 140 and ground reaction forces acting on foot 120 may not be needed to determine an ankle joint torque when foot 120 is not in contact with the ground.

According to one embodiment of the present invention, motion execution is relegated to voluntary commands from the CNS, wherein the CNS can be assigned the role of issuing the commands to generate a desired motion. These commands are in the form of neural signals that activate the muscles to generate muscle torques required to produce a desired motion.

One embodiment of the present invention determines 406 an ankle joint torque to compensate for a ground reaction force acting on foot 120 by setting the ground reaction moment, velocity and acceleration terms in equations 13-15 to zero, as shown in equations 34-38. For example, a linear velocity or acceleration associated with the foot can be set to zero when determining the ankle joint torque. To provide another example, an angular velocity or acceleration associated with the foot can be set to zero when determining the ankle joint torque. As shown in equation 39, according to one embodiment the effect of gravitational forces due to foot 120 can also be ignored. According to one embodiment of the present invention, the ankle joint torque determined in step 406 can be used to control an ankle-foot orthosis.

$${}^1N_{gr} = 0 \tag{34}$$

$$\dot{\Theta}_1 = 0 \tag{35}$$

$$W_1 = 0 \tag{36}$$

$$\dot{W}_1 = 0 \tag{37}$$

$$\ddot{X}_1 = 0 \tag{38}$$

$$m_1 g = 0 \tag{39}$$

According to one embodiment of the present invention, based on equations 13-15 and the constraints in equations 34-39, an ankle joint torque to compensate for the ground reaction forces acting on foot 120 can be determined 406 using equation 40. The ground reaction forces can be obtained, for example, by measurement or estimation.

$${}^1N_{AJT_{III}} = {}^1R_o \tilde{L}_{D1} \Gamma_{gr} - {}^1R_o \tilde{L}_{P1} \Gamma_{gr} \tag{40}$$

According to one embodiment of the present invention, equation 40 can be written as equation 42 by using the simplification in equation 41.

$$L = L_{D1} - L_{P1} \tag{41}$$

$${}^1N_{AJT_{III}} = {}^1R_o \tilde{L} \Gamma_{gr} \tag{42}$$

If the segment lengths are expressed in the body-fixed coordinate system, for example in online control of an ankle-foot orthosis, equation 42 can be written as equation 43. Equation 43 can be used to determine 406 an ankle joint torque to compensate for ground reaction forces acting on foot 120 according to one embodiment of the present invention.

$$^I N_{AJT_{III}} = {}^1\tilde{L} \, {}^1R_o \Gamma_{gr} \tag{43}$$

According to one embodiment, not every degree of freedom is actuated because it is not always necessary to have a motorized actuator at every degree of freedom of the ankle joint 100. Let $^1\hat{S}$ define a unit vector in the direction of an axis of rotation, for example the flexion/extension axis, referred to the foot reference frame. Based on equation 43, the actuator control to compensate for a component of a ground reaction force about an axis of rotation is given by equation 44. According to one embodiment of the present invention, online control of an ankle-foot orthosis can be achieved by using real time Euler angles to obtain the rotation matrix, as shown in equations 1-2 above.

$$U_{AJT_{III}} = {}^1N_{AJT_{III}} \cdot {}^1\hat{S} \tag{44}$$

For an actuated degree of freedom, it sometimes may not be desirable to generate an assist torque that fully compensates for ground reaction forces. One embodiment of the present invention determines an ankle joint torque for partial compensation using an assist ratio that actuates a fraction of the total torque at ankle joint 100. According to one embodiment of the present invention, an ankle joint torque for partial compensation of a degree of freedom can be determined by pre-multiplying equation 44 with an assist ratio a as shown in equation 45. The assist ratio a can have a value between zero and one for partial assist, a value of zero for no assist, and a value of one for full assist of an actuated degree of freedom.

$$\tau_{AJT_{III}} = a \, {}^1N_{AJT_{III}} \cdot {}^1\hat{S} \tag{45}$$

As shown in equations 40-45 above, one embodiment of the present invention determines 406 an ankle joint torque to compensate for sheer components such as $\Gamma_{gr}(x)$, $\Gamma_{gr}(y)$ as well as vertical components $\Gamma_{gr}(z)$ of a ground reaction force. Another embodiment of the present invention determines 406 an ankle joint torque to compensate for one or more sheer components of a ground reaction force in equations 40-45, without compensating for vertical components of the ground reaction force.

One embodiment of the present invention determines 406 an ankle joint torque to compensate for one or more vertical components of a ground reaction force in equations 40-45, without compensating for sheer components of the ground reaction force. For example, a sheer component of a ground reaction force that is not readily available can be ignored by setting it to zero in equations 40-45.

According to one embodiment of the present invention a static component of the vertical ground reaction force as well as a dynamic component of the vertical ground reaction force can be used to determine an ankle joint torque. In some instances, for example in the double support phase of motion, the static component may not be readily obtainable. One embodiment of the present invention determines 406 an ankle joint torque that compensates for vertical components of a ground reaction force acting on the foot by using the dynamic component of the vertical ground reaction force in place of the ground reaction force $\Gamma_{gr}$ in equations 40-45. For example, an ankle joint torque that compensates for the dynamic component of the vertical ground reaction force acting on foot 120 can be determined using equations 42-45. The dynamic component of the vertical ground reaction force is available, for example, by using force and pressure sensors such as in-shoe force and pressure sensors.

Referring to equations 40-45, according to one embodiment of the present invention the ankle joint torque for controlling an ankle-foot orthosis can be determined without the need for online measurement information, for example if the orientation of the foot 120 is known a priori and is identical to the orientation of the foot coordinate system at run-time and/or if the ground reaction force is constant, known a priori and identical to the ground reaction force at run-time.

Embodiments of the present invention shown in equations 25-33 and 40-45 do not require sophisticated sensory inputs because readily-obtained information, for example the mass of foot 120, is sufficient to determine the ankle joint torque for control of an ankle-foot orthosis. In some embodiments, the orientation of foot 120 and the ground reaction force may be required. Further, since joint torques in equations 25-33 and 40-45 can be determined as a function of joint positions and orientations and do not contain velocity or acceleration terms, one embodiment of the present invention is not sensitive to noise amplification from numerical differentiation of noisy kinematic variables.

Simulation Results for an Ankle Foot Orthosis

Standard gait measurements including motion capture and force plate data were obtained courtesy of Christopher L. Vaughan, Brian Davis, and Jeremy C. O'Connor, Dynamics of Human Gait, Kiboho Publishers, Cape town South Africa, 2d ed., 1999, which is incorporated by reference herein in its entirety. The recorded motion from a Helen Hayes marker set and a series of anthropometric measurements were used as inputs to a set of statistical regression equations to determine the foot segment parameters and ankle joint center. See Vaughan et al., Dynamics of Human Gait. The Euler angles and center of gravity of the foot were calculated. The method proposed by Grood & Suntay and adopted by Vaughan et al. for human gait analysis was used to determine the platerflexion/dorsiflexion axis of rotation. See E. S. Grood and W. J. Suntay, A joint coordinate system for the clinical description of three dimensional motions: Application to the knee, Journal of Biomechanical Engineering, 105:136-144, 1983, which is incorporated by reference herein in its entirety.

Figure 5:
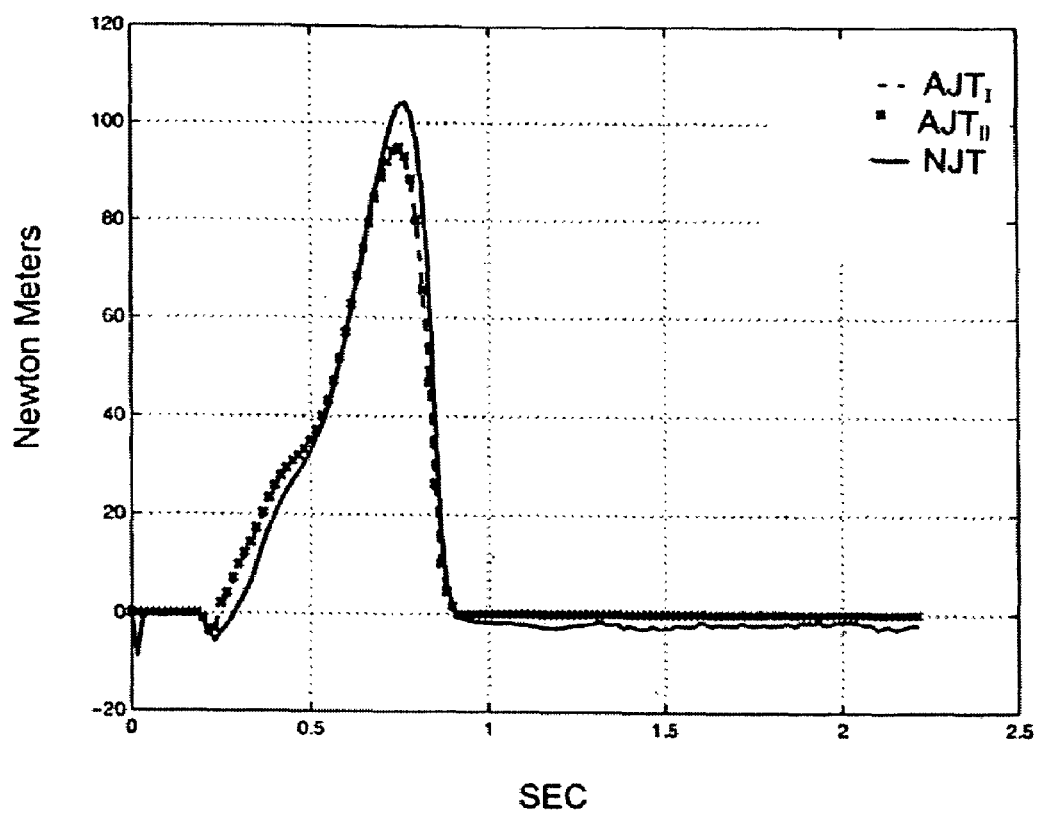
FIG. 5 is a graph comparing the ankle assist torque for planterflexion/dorsiflexion of the ankle during a simulated cycle of gait according to various embodiments of the present invention.

FIG. 5 is a graph comparing the ankle assist torque for planterflexion/dorsiflexion of the ankle during a simulated cycle of gait according to various embodiments of the present invention. Referring to FIG. 5, NJT represents the net joint torque for inverse dynamics control determined using equation 17 above, which is calculated based on complete sensory and complete model information and which therefore represents the total torque required by the muscles to perform this task. $AJT_I$ represents an ankle joint torque to compensate for the vertical component of the ground reaction force and the gravitational force due to foot 120, determined using equation 29 above, according to one embodiment of the present invention. Similarly, $AJT_{II}$ represents an ankle joint torque to compensate for the vertical component of the ground reaction force, determined using equation 32 above, according to one embodiment of the present invention. Note that $AJT_I$ and $AJT_{II}$ use partial sensory and partial model information. FIG. 5 shows that the ankle joint torques determined using equations 29 and 32 account for the majority of the total torque required during this task, wherein the total torque is given by equation 17 above.

Figure 6:
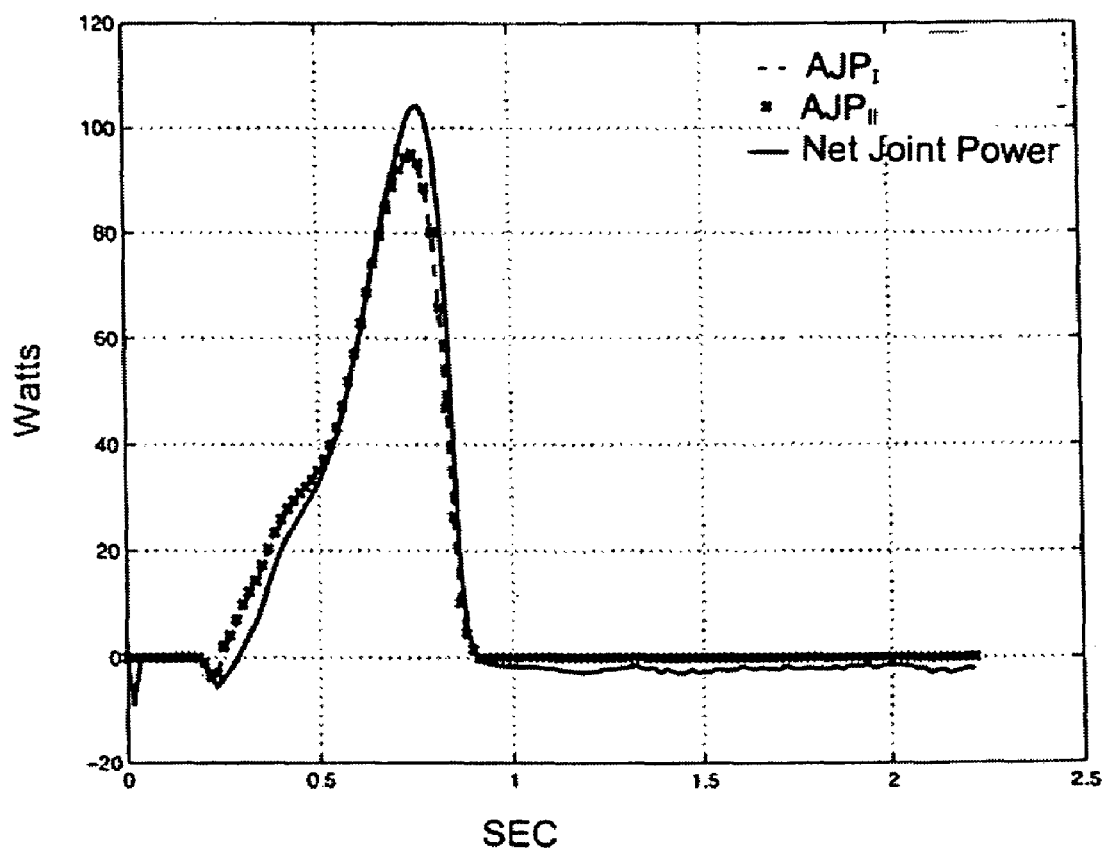
FIG. 6 is a graph comparing the ankle assist power during a simulated cycle of gait according to various embodiments of the present invention.
Figure 7A:
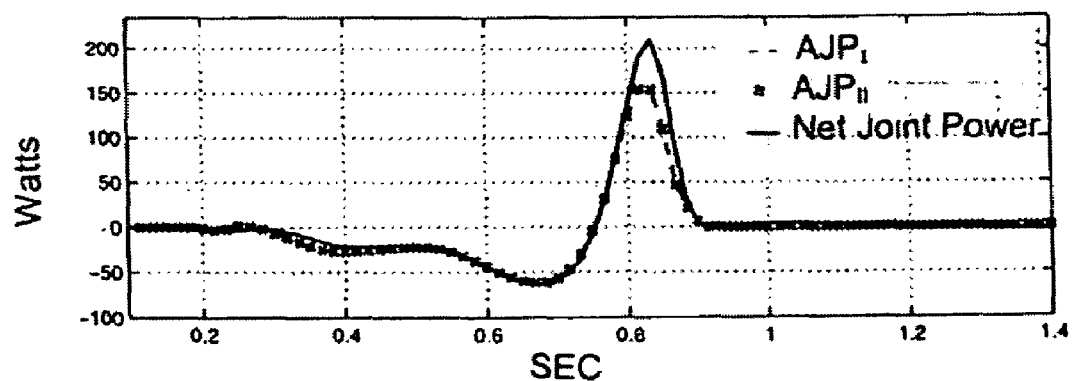
FIG. 7A is a graph showing the ankle assist power during a simulated cycle of gait according to various embodiments of the present invention.

FIG. 6 is a graph comparing the ankle assist power during a simulated cycle of gait according to various embodiments of the present invention. As shown in equations 46-48, the graphs for Net Joint Power (NJP), $AJP_I$, and $AJP_{II}$ in FIGS. 6 and 7A are obtained by the inner product of joint reaction moments and the angular velocity $w_1$ of the foot. Referring to equation 46, NJP represents the net joint power for inverse dynamics control, which is calculated based on complete sensory and complete model information and which therefore represents the total power required by the muscles to perform this task. In equation 46, the term $^0N_a^T$ is derived using equations 13-15 above. Referring to equation 47, $AJP_I$ represents an ankle joint power to compensate for the vertical component of the ground reaction force and the gravitational force due to foot 120 according to one embodiment of the present invention. In equation 47, the term $^1N_{AJT_I}^T$ is determined as shown in equation 28 above. Referring to equation 48, $AJP_{II}$ represents an ankle joint power to compensate for the vertical component of the ground reaction force according to one embodiment of the present invention. In equation 48, the term $^1N_{AJT_{II}}^T$ is determined as shown in equations 31 above. Note that $AJP_I$ and $AJP_{II}$ use partial sensory and partial model information. FIG. 6 provides further evidence that compensating for ground reaction forces and gravitational forces provides a majority of the ankle joint power required to decelerate the body during heel strike as well as a majority of the propulsive power required at the ankle during toe-off.

$$NJP = {}^0N_a^{T0} w_1 \quad (46)$$

$$AJP_I = {}^1N_{AJT_I}^{T1} w_1 \quad (47)$$

$$AJP_{II} = {}^1N_{AJT_{II}}^{T1} w_1 \quad (48)$$

Figure 7B:
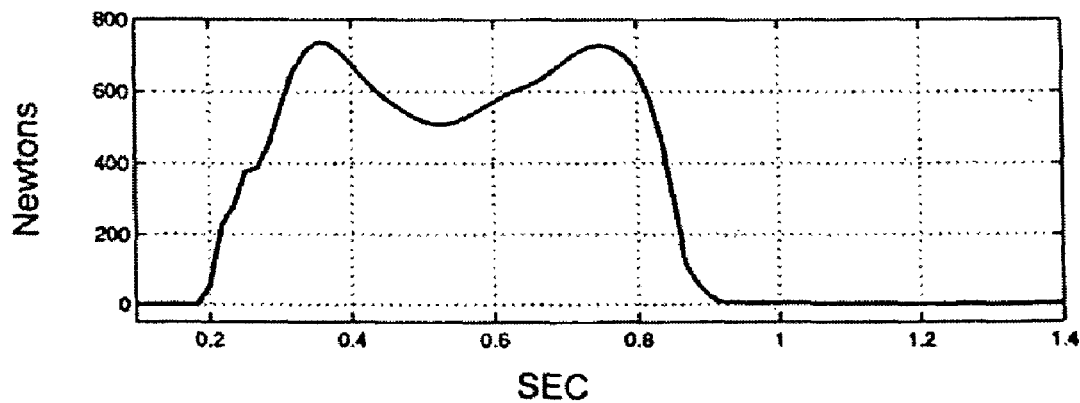
FIG. 7B is a graph showing the vertical component of the ground reaction force during a simulated cycle of gait according to one embodiment of the present invention.

FIG. 7A shows the ankle assist power according to various embodiments of the present invention, which can be compared with the vertical component of the ground reaction force during a simulated cycle of gait, shown in FIG. 7B. Heel strike occurs at approximately t=0.2 sec, at which the vertical ground reaction force goes from zero to a positive number. Toe-off occurs at approximately t=0.9 sec, at which the vertical ground reaction force returns to zero. The simulation results shown in FIGS. 5-7 concur with our expectation that compensating for ground reaction forces and or gravitational forces plays a major role in contributing to ankle power required for gait.

One embodiment of the present invention provides a system for automatically controlling an ankle-foot orthosis at an ankle joint, comprising first receiving means for receiving a system parameter, second receiving means for receiving an orientation of a foot connected to the ankle joint, and first determining means for determining a joint torque for controlling the ankle-foot orthosis to compensate for a component of a ground reaction force acting on the foot, wherein the ankle-foot orthosis is an active ankle-foot orthosis. According to one embodiment of the present invention, the system further comprises second determining means for determining a joint torque to compensate for the component of the ground reaction force about an axis of rotation of the ankle-foot orthosis. According to a further embodiment, the system further comprises second determining means for determining a joint torque to provide partial compensation for the component of the ground reaction force acting on the foot.

The present invention may be embodied in various forms and should not be construed as limited to the embodiments set forth herein. Rather, these embodiments are provided so that disclosure will be thorough and complete and will fully convey the invention to those skilled in the art. Further, the apparatus and methods described are not limited to rigid bodies.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without department from the spirit and scope of the invention as it is defined in the appended claims.

What is claimed is:

1. A computer based method of controlling a human-exoskeleton system comprising an ankle-foot orthosis at an ankle joint, the method comprising:
   receiving a system parameter for the human-exoskeleton system;
   receiving an orientation of a foot connected to the ankle joint;
   determining a control torque for controlling the ankle-foot orthosis to compensate for a component of a ground reaction force acting on the foot, the control torque determined by setting a value of one of a linear velocity associated with the foot and a linear acceleration associated with the foot to zero and
   controlling the ankle-foot orthosis according to the control torque to compensate for the component of the ground reaction force acting on the foot.

2. A computer based method of controlling a human-exoskeleton system comprising an ankle-foot orthosis at an ankle joint, the method comprising:
   receiving a system parameter for the human-exoskeleton system;
   receiving an orientation of a foot connected to the ankle joint;
   determining a control torque for controlling the ankle-foot orthosis to compensate for a component of a ground reaction force acting on the foot, the control torque determined by setting a value of one of an angular velocity associated with the foot and an angular acceleration associated with the foot to zero and
   controlling the ankle-foot orthosis according to the control torque to compensate for the component of the ground reaction force acting on the foot.

3. The method of claim 1, further comprising determining the control torque for controlling the ankle-foot orthosis to compensate for the component of the ground reaction force about an axis of rotation of the ankle-foot orthosis.

4. The method of claim 1, further comprising determining the control torque for controlling the ankle-foot orthosis to provide partial compensation for the component of the ground reaction force acting on the foot.

5. The method of claim 1, wherein no online measurement information is needed to determine the control torque for controlling the ankle-foot orthosis.

6. A computer based method of controlling a human-exoskeleton system comprising an ankle-foot orthosis at an ankle joint, the method comprising:
   receiving a system parameter for the human-exoskeleton system;
   receiving an orientation of a foot connected to the ankle joint;
   determining a control torque for controlling the ankle-foot orthosis to compensate for a vertical component of a force acting on the foot; and
   controlling the ankle-foot orthosis according to the control torque to compensate for the vertical component of the force acting on the foot.

7. The method of claim 6, wherein the vertical component of the force acting on the foot comprises one of:

a force due to gravity acting on the foot; and a vertical component of a ground reaction force acting on the foot.

8. The method of claim 6, wherein the vertical component of the ground reaction force is measured using one of:

a force sensor; and a pressure sensor.

9. A system for automatically controlling an ankle-foot orthosis at an ankle joint, comprising:

first receiving means for receiving a system parameter;

second receiving means for receiving an orientation of a foot connected to the ankle joint; and first determining means for determining a control torque for controlling the ankle-foot orthosis to compensate for a component of a ground reaction force acting on the foot, the control torque determined by setting a value of one of a linear velocity associated with the foot and a linear acceleration associated with the foot to zero.

10. The system of claim 9, wherein the component of the ground reaction force comprises a vertical component of the ground reaction force.

11. The system of claim 9, wherein the component of the ground reaction force comprises a dynamic component of a vertical ground reaction force.

12. The system of claim 9, further comprising second determining means for determining the control torque for controlling the ankle-foot orthosis to compensate for the component of the ground reaction force about an axis of rotation of the ankle-foot orthosis.

13. The system of claim 9, further comprising second determining means for determining the control torque for controlling the ankle-foot orthosis to provide partial compensation for the component of the ground reaction force acting on the foot.

14. The method of claim 2, further comprising determining the control torque for controlling the ankle-foot orthosis to compensate for the component of the ground reaction force about an axis of rotation of the ankle-foot orthosis.

15. The method of claim 2, further comprising determining the control torque for controlling the ankle-foot orthosis to provide partial compensation for the component of the ground reaction force acting on the foot.

16. The method of claim 2, wherein no online measurement information is needed to determine the control torque for controlling the ankle-foot orthosis.

17. A system for automatically controlling an ankle-foot orthosis at an ankle joint, comprising:

first receiving means for receiving a system parameter;

second receiving means for receiving an orientation of a foot connected to the ankle joint; and first determining means for determining a control torque for controlling the ankle-foot orthosis to compensate for a component of a ground reaction force acting on the foot, the control torque determined by setting a value of one of an angular velocity associated with the foot and an angular acceleration associated with the foot to zero.

18. The system of claim 17, wherein the component of the ground reaction force comprises a vertical component of the ground reaction force.

19. The system of claim 17, wherein the component of the ground reaction force comprises a dynamic component of a vertical ground reaction force.

20. The system of claim 17, further comprising second determining means for determining the control torque for controlling the ankle-foot orthosis to compensate for the component of the ground reaction force about an axis of rotation of the ankle-foot orthosis.

21. The system of claim 17, further comprising second determining means for determining the control torque for controlling the ankle-foot orthosis to provide partial compensation for the component of the ground reaction force acting on the foot.

* * * * *

UNITED STATES PATENT AND TRADEMARK OFFICE
CERTIFICATE OF CORRECTION

PATENT NO. : 7,650,204 B2
APPLICATION NO. : 11/402487
DATED : January 19, 2010
INVENTOR(S) : Behzad Dariush It is certified that error appears in the above-identified patent and that said Letters Patent is hereby corrected as shown below:

On the Title page under Related U.S. Application Data, delete existing Item (63) and Item (60) in their entirety and replace with the following:

Continuation-in-part of application No. 11/395,654, filed on Mar. 30, 2006, which is a continuation-in-part of application No. 11/038,691, filed on Jan. 19, 2005, which is a continuation-in-part of application No. 11/038,692, filed on Jan. 19, 2005, which is a continuation-in-part of application No. 11/038,978, filed on Jan. 19, 2005, and a continuation of application No. 10/151,647, filed on May 16, 2002. U.S. Application No. 11/395,654, filed March 30, 2006, is also a continuation-in-part of U.S. patent application No. 10/824,059 filed on April 13, 2004, which is a continuation-in part of U.S. patent application No. 10/655,460 filed on September 5, 2003, which claims priority under 35 U.S.C §119(e) from U.S. provisional applications No. 60/484,708 filed on July 3, 2003, No. 60/421,964 filed on October 28, 2002, and No. 60/413,024 filed on September 23, 2002. U.S. patent application No. 11/395,654, filed on March 30, 2006, is also a continuation-in-part of U.S. patent application No. 10/280,771 filed on October 25, 2002, which claims priority under 35 U.S.C §119(e) from U.S. provisional applications No. 60/330,689 filed on October 29, 2001, and No. 60/333,753 filed on November 29, 2001.

Provisional application No. 60/667,518, filed on Apr. 1, 2005, provisional application No. 60/670,732, filed on Apr. 12, 2005, provisional application No. 60/301,891, filed on Jun. 29, 2001, provisional application No. 60/353,378, filed on Jan. 31, 2002.

In the Specifications:

Column 1, after "Cross-Reference to Related Applications," delete lines 7 thru 48 in their entirety, and replace with the following:

Signed and Sealed this
Twentieth Day of August, 2013

Teresa Stanek Rea
*Acting Director of the United States Patent and Trademark Office*

CERTIFICATE OF CORRECTION (continued)
U.S. Pat. No. 7,650,204 B2

This application is a continuation-in-part of U.S. patent application No. 11/395,654, filed on March 30, 2006, and entitled "An Exoskeleton Controller for a Human-Exoskeleton System," which claims priority under 35 U.S.C §119(e) from U.S. provisional applications No. 60/667,518 filed on April 1, 2005, and No. 60/670,732 filed on April 12, 2005, and which is a continuation-in-part of U.S. patent applications No. 11/038,691 filed on January 19, 2005, No. 11/038,692 filed on January 19, 2005, and No. 11/038,978 filed on January 19, 2005, which are all incorporated by reference herein in their entirety. U.S. patent applications No. 11/038,691 filed on January 19, 2005, No. 11/038,692 filed on January 19, 2005, and No. 11/038,978 filed on January 19, 2005, are each a continuation-in-part of U.S. patent application No. 10/151,647 filed on May 16, 2002, which claims priority under 35 U.S.C §119(e) from U.S. provisional applications No. 60/301,891 filed on June 29, 2001, and No. 60/353,378 filed on January 31, 2002, which are all incorporated by reference herein in their entirety.

U.S. patent application No. 11/395,654, filed on March 30, 2006, and entitled "An Exoskeleton Controller for a Human-Exoskeleton System," is also a continuation-in-part of U.S. patent application No. 10/824,059 filed on April 13, 2004, which is a continuation-in part of U.S. patent application No. 10/655,460 filed on September 5, 2003, which claims priority under 35 U.S.C §119(e) from U.S. provisional applications No. 60/484,708 filed on July 3, 2003, No. 60/421,964 filed on October 28, 2002, and No. 60/413,024 filed on September 23, 2002, which are all incorporated by reference herein in their entirety. U.S. patent application No. 11/395,654, filed on March 30, 2006, and entitled "An Exoskeleton Controller for a Human-Exoskeleton System," is also a continuation-in-part of U.S. patent application No. 10/280,771 filed on October 25, 2002, which claims priority under 35 U.S.C §119(e) from U.S. provisional applications No. 60/330,689 filed on October 29, 2001, and No. 60/333,753 filed on November 29, 2001, which are all incorporated by reference herein in their entirety.